United States Patent
Brands et al.

(10) Patent No.: US 6,469,164 B2
(45) Date of Patent: Oct. 22, 2002

(54) PROCESS FOR THE SYNTHESIS OF (2R, 2-ALPHA-R)-4-BENZYL-2-[1-(3,5-BIS(TRIFLUOROMETHYL)PHENYL)ETHOXY]-1,4-OXAZINE-3-ONE

(75) Inventors: Karel M. Jos Brands, Jersey City, NJ (US); Joseph F. Payack, Somerset, NJ (US); Philip J. Pye, Guttenberg, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/878,033

(22) Filed: Jun. 8, 2001

(65) Prior Publication Data

US 2002/0052493 A1 May 2, 2002

Related U.S. Application Data (60) Provisional application No. 60/210,255, filed on Jun. 8, 2000.

(51) Int. Cl.$^7$ .............................................. C07D 265/32
(52) U.S. Cl. ...................................................... 544/174
(58) Field of Search ........................................... 544/174

(56) References Cited

PUBLICATIONS

Wang et al, Chemical Abstracts, vol. 134:198170 (2000).*

* cited by examiner

*Primary Examiner*—John M. Ford
(74) *Attorney, Agent, or Firm*—J. Eric Thies; Melvin Winokur (57) ABSTRACT

The present invention is concerned with novel processes for the preparation of (2R, 2-alpha-R)-4-benzyl-2-[1-[3,5-bis(trifluoromethyl)phenyl]ethoxy-1,4-oxazin-3-one. This compound is useful as an intermediate in the synthesis of compounds which possess pharmacological activity.

8 Claims, 1 Drawing Sheet

FIG. 1

PROCESS FOR THE SYNTHESIS OF (2R, 2-ALPHA-R)-4-BENZYL-2-[1-(3,5-BIS(TRIFLUOROMETHYL)PHENYL)ETHOXY]-1,4-OXAZINE-3-ONE

CROSS REFERENCE TO RELATED APPLICATIONS

This application claims the benefit of Provisional Application No. 60/210,255, filed Jun. 8, 2000.

BACKGROUND OF THE INVENTION

The present invention relates to processes for the preparation of (2R, 2-alpha-R)-4-benzyl-2-[1-[3,5-bis(trifluoromethyl)phenyl]ethoxy-1,4-oxazin-3-one which is useful as an intermediate in the preparation of certain therapeutic agents. In particular, the present invention provides a process for the preparation of (2R, 2-alpha-R)-4-benzyl-2-[1-[3,5-bis(trifluoromethyl)phenyl]ethoxy-1,4-oxazin-3-one which is an intermediate in the synthesis of pharmaceutical compounds which are substance P (neurokinin-1) receptor antagonists.

The preparation of (2R, 2-alpha-R)-4-benzyl-2-[1-[3,5-bis(trifluoromethyl)phenyl]ethoxy-1,4-oxazin-3-one has not been previously disclosed and the present invention provides effective methodology for the preparation of (2R, 2-alpha-R)-4-benzyl-2-[1-[3,5-bis(trifluoromethyl)phenyl]ethoxy-1, 4-oxazin-3-one in relatively high yield and purity.

It will be appreciated that (2R, 2-alpha-R)-4-benzyl-2-[1-[3,5-bis(trifluoromethyl)phenyl]ethoxy-1,4-oxazin-3-one is an important intermediate for a particularly useful class of therapeutic agents. As such, there is a need for the development of a process for the preparation of (2R, 2-alpha-R)-4-benzyl-2-[1-[3,5-bis(trifluoromethyl)phenyl]ethoxy-1,4-oxazin-3-one which is readily amenable to scale-up, uses cost-effective and readily available reagents and which is therefore capable of practical application to large scale manufacture.

Accordingly, the subject invention provides a process for the preparation of (2R, 2-alpha-R)-4-benzyl-2-[1-[3,5-bis(trifluoromethyl)phenyl]ethoxy-1,4-oxazin-3-one via a very simple, short, relatively inexpensive and highly efficient synthesis.

SUMMARY OF THE INVENTION

The present invention concerns (2R, 2-alpha-R)-4-benzyl-2-[1-[3,5-bis(trifluoromethyl)phenyl]ethoxy-1,4-oxazin-3-one and processes for the preparation therof. The present invention further relates to novel processes for the preparation of a compound of the formula:

This compound is an intermediate in the synthesis of compounds which possess pharmacological activity. In particular, such compounds are substance P (neurokinin-1) receptor antagonists which are useful e.g., in the treatment of psychiatric disorders, inflammatory diseases, and emesis.

DETAILED DESCRIPTION OF THE INVENTION

The present invention concerns (2R, 2-alpha-R)-4-benzyl-2-[1-[3,5-bis(trifluoromethyl)phenyl]ethoxy-1,4-oxazin-3-one of the formula:

and processes for the preparation thereof.

A preferred embodiment of the general process for the preparation of (2R, 2-alpha-R)-4-benzyl-2-[1-[3,5-bis(trifluoromethyl)phenyl]ethoxy-1 ,4-oxazin-3-one is as follows:

Activating agent

Lewis acid

Base

(wherein X is selected from: —F, —Cl, —Br, —I, —O—CO—CF$_3$, —O—CO—CCl$_3$, —CN—Cl$_3$ and —O—COR wherein is C$_{1-6}$alkyl, substituted C$_{1-6}$alkyl, phenyl or substituted phenyl).

In accordance with the present invention, the treatment of 4-benzyl-2-hydroxy-1,4-oxazin-3-one under the subject conditions provides (2R, 2-alpha-R)-4-benzyl-2-[1-[3,5-bis(trifluoromethyl)phenyl]ethoxy-1,4-oxazin-3-one in high yields and in an efficient route.

Another embodiment of the present invention concerns a process for the preparation of (2R, 2-alpha-R)-4-benzyl-2-[1-[3,5-bis(trifluoromethyl)phenyl]-ethoxy-1,4-oxazin-3-one of the formula:

which comprises:
 activation of the 2-hydroxy group of 4-benzyl-2-hydroxy-1,4-oxazin-3-one of the formula:

coupling of the activated 4-benzyl-2-hydroxy-1,4-oxazin-3-one with (R)-1-[3,5-bis(trifluoromethyl)-phenyl]ethan-1-ol of the formula:

in the presence of a Lewis acid; and crystallization driven epimerization of the anomeric center, to give (2R, 2-alpha-R)-4-benzyl-2-[1-[3,5-bis(trifluoromethyl)phenyl]ethoxy-1,4-oxazin-3-one.

Activation of the 2-hydroxy group of 4-benzyl-2-hydroxy-1,4-oxazin-3-one is conducted via reaction with:

a halogenating agent to provide derivatives wherein X is F, Cl, Br, or I, trichloroacetonitrile to provide the corresponding trichloroimidate (X is —CNCl$_3$), or an optionally substituted alkyl or aryl acid chloride or acid anhydride to provide the corresponding optionally substituted ester (wherein X is —O—CO—R or —O—COCF$_3$ or —O—COCCl$_3$ wherein R is C$_{1-6}$alkyl, substituted C$_{1-6}$alkyl, phenyl or substituted phenyl).

Preferred activating conditions employ trifluoroacetic anhydride in acetonitrile. Activation is typically carried out at a reaction temperature between about −20 and about 20° C.

Coupling of the activated lactam with (R)-1-[3,5-bis(trifluoromethyl)-phenyl]ethan-1-ol is catalyzed by a Lewis Acid to provide a mixture of (R,S) and (R,R) 4-benzyl-2-[1-[3,5-bis(trifluoromethyl)phenyl]ethoxy-1,4-oxazin-3-ones in an approximate 1/1 ratio. Alternatively, activated lactams wherein X is F, Cl, Br or I may be reacted with (R)-1-[3,5-bis(trifluoromethyl)phenyl]ethan-1-ol in the presence of a base. The Lewis acid is selected from boron trifluoride etherate, TMSOTf, titanium tetrachloride, tin tetrachloride, and the like. The solvent is typically a polar aprotic solvent selected from acetonitrile, dimethylformamide, ethyl acetate, tetrahydrofuran, toluene, dichloromethane and the like. A preferred solvent is acetonitrile. The reaction is typically carried out at a temperature range of between about −50 and about 50° C.

Crystallization driven epimerization of the anomeric center is conducted using a base. Continuous crystallization of the desired (2R, 2-alpha-R)-4-benzyl-2-[1-[3,5-bis(trifluoromethyl)phenyl]ethoxy-1,4-oxazin-3-one diastereomer allows essentially complete conversion of the initial 1/1 mixture of diastereomers to the desired isomer. The epimerization may be achieved with a base selected from potassium or sodium hydroxides or alkoxides in an alcohol and a cosolvent. For high yields in the epimerization it is preferred that the alcohol and the cosolvent provide relatively non-polar conditions. The alkoxides can be derived from lower (C$_1$–C$_5$) or higher (>C$_6$) primary, secondary or tertiary alcohols. The preferred alcohols are lipophilic tertiary alcohols. The most preferred alcohol is 3,7-dimethyloctan-3-ol (tetrahydrolinalool) and the most preferred base is the potassium salt of 3,7-dimethyloctan-3-ol. The cosolvent is typically a non-polar C$_5$–C$_{12}$ alkane. The most preferred cosolvents are hexane or heptane. The reaction is typically carried out at a temperature range of between about −20 and about 25° C. The most preferred temperature range is between about −10 and about 0° C.

In a preferred embodiment, the present invention is directed to a process for the preparation of (2R, 2-alpha-R)-4-benzyl-2-[1-[3,5-bis(trifluoromethyl)phenyl]ethoxy-1,4-oxazin-3-one which comprises reacting 4-benzyl-2-hydroxy-1,4-oxazin-3-one and (R)-1-[3,5-bis(trifluoromethyl)-phenyl]ethan-1-ol under the aforementioned conditions.

A specific embodiment of the present invention concerns a process for the preparation of (2R, 2-alpha-R)-4-benzyl-2-[1-[3,5-bis(trifluoromethyl)phenyl]- ethoxy-1,4-oxazin-3-one of the formula:

which is outlined as follows:

-continued

In the present invention, it is preferred that the activating agent is trifluoroacetic anhydride.

In the present invention, it is preferred that the Lewis acid is boron trifluoride etherate.

In the present invention, the preferred solvent for the activation and coupling is acetonitrile.

In the present invention, it is preferred that the base is selected from: potassium 3,7-dimethyloct-3-oxide and potassium t-butoxide.

In the present invention, the preferred solvent for the epimerization/crystallization is a mixture of 3,7-dimethyloctan-3-ol and heptane.

In the present invention, it is preferred that the temperature of the reaction mixture is between about 0° C. to about 25° C. for the activation, 25° C. to about 30° C. for the coupling and about –10° C. to about –5° C. for the epimerization/crystallization.

Highly preferred reaction conditions for the subject process are outlined below.

Activation

Reaction of the lactol with trifluoroacetic anhydride gives the lactol trifluoroacetate and one equivalent of trifluoroacetic acid. The reaction is preferably run in cold (–5 to 5° C.) acetonitrile at ~2.5 mL/g (KF<100 ppm). An exact trifluoroacetic anhydride charge (100 mol %) is preferable, along with a rapid addition rate. The solution, which generally exhibits an exotherm to 25–35° C., may be allowed to cool to 20 to 25° C. and then aged for about 1 hour.

Coupling

Addition of 90–105 mol % of (R)-1-[3,5-bis (trifluoromethyl)phenyl]- ethan-1-ol and 10–50 mol % of borontrifluoride etherate to the lactol trifluoroacetate solution results in a coupling reaction. The mixture is generally aged for 3–5 hours at between about 20–30° C. to achieve complete conversion. The solution may be quenched into a chilled solution of 5N aqueous sodium hydroxide. A workup procedure provides a 1/1 mixture of diastereomers as a solution in heptane and 3,7-dimethyloctan-3-ol.

Epimerization/crystallization

Two similar protocols were developed for this step. Upon cooling to between –10 and –5° C. and seeding of the dry heptane/3,7-dimethyloctan-3-ol solution the desired (R,R) diastereomer crystallizes. The first protocol uses 70 mol % of the more readily available potassium tert-butoxide and 300 mol % of 3,7-dimethyloctan-3-ol. After approximately 8 hours under these conditions virtually all of the undesired (R,S) diastereomer has been converted to crystalline (R,R) diastereomer. The second protocol uses 110 mol % of 3,7-dimethyloctan-3-ol and 30 mol % of the corresponding potassium salt. Complete conversion under these conditions is achieved after approximately 5 hours. The faster conversion and higher concentrations in the second protocol result in a much higher productivity which makes this protocol the most preferred one. After either protocol the product can be isolated directly via filtration or, alternatively, the slurry is quenched with acetic acid and subjected to an aqueous workup (temperatures maintained between 10–60° C. to solubilize the product) to remove salts.

Optional Recrystallization

After the optional solubilization of the product and aqueous workup to remove salts, pure (2R, 2-alpha-R)-4-benzyl-2-[1-[3,5-bis(trifluoromethyl)phenyl]-ethoxy-1,4-oxazin-3-one can be crystallized by cooling the solution between –10 and 0° C. The product can be isolated via a filtration.

The present invention is further directed to the compound (2R, 2-alpha-R)-4-benzyl-2-[1-[3,5-bis(trifluoromethyl) phenyl]ethoxy-1,4-oxazin-3-one of the formula:

As used herein, a polymorphic form of a chemical compound is the same chemical entity, but in a different crystalline arrangement. A preferred polymorphic form of (2R, 2-alpha-R)-4-benzyl-2-[1-[3,5-bis(trifluoromethyl)-phenyl]ethoxy-1,4-oxazin-3-one is described herein. This polymorphic form has advantages over the other known forms of (2R, 2-alpha-R)-4-benzyl-2-[1-[3,5-bis(trifluoromethyl)-phenyl]ethoxy-1,4-oxazin-3-one in terms of thermodynamic stability and processability.

The (2R, 2-alpha-R)-4-benzyl-2-[1-[3,5-bis(trifluoromethyl)-phenyl]ethoxy-1,4-oxazin-3-one obtained in accordance with the present invention may be used as starting material in further reactions directly or following purification.

The starting materials and reagents for the subject processes are either commercially available or are known in the literature or may be prepared following literature methods described for analogous compounds. The skills required in carrying out the reaction and purification of the resulting reaction products are known to those in the art. Purification procedures include crystallization, distillation, normal phase or reverse phase chromatography.

The following examples are provided for the purpose of further illustration only and are not intended to be limitations on the disclosed invention.

EXAMPLE 1

4-Benzyl-2-hydroxy-1,4-oxazin-3-one

| Materials | MW | Density | Amount | mol | Equiv. |
|---|---|---|---|---|---|
| N-Benzylethanolamine (96%) | 151.21 | 1.065 | 7.80 kg | 49.5 (assay) | 1.0 |
| Glyoxylic acid (50% in water) | 74.04 | 1.342 | 12.60 L | 114.2 | 2.31 |
| Tetrahydrofuran | 72.11 | 0.889 | 27.0 L | — | — |
| 4-Benzyl-2-hydroxy-1,4-oxazin-3-one seed | 207.23 | — | 0.252 kg | 1.24 | 0.025 |
| Water | 18.0 | 1.00 | 63.0 L | — | — |

A solution of THF (27.0 L) and 50% aqueous glyoxylic acid (12.6 L; 16.9 kg) was heated to reflux and N-benzylethanolamine (7.8 kg) was added over 45 min. The resulting mixture was refluxed for 21 h. Then the THF was distilled under atmospheric pressure while maintaining a constant volume by simultaneous addition of water (27 L). Upon completion of the distillation (<8 vol % of THF in batch) the mixture was cooled from approximately 95–100 to 79–81° C. and was optionally seeded with 4-benzyl-2-hydroxy-1,4-oxazin-3-one (250 g). Upon further cooling to room temperature the product crystallized. Crystalline 4-benzyl-2-hydroxy-1,4-oxazin-3-one was filtered, washed with water and then dried in a vacuum oven at about 60° C. under a stream of $N_2$ (72–76% yield); m.p. 134° C.

$^1$H NMR (400 MHz, $CDCl_3$) δ3.11 (ddd, J=12.5, 3.6 2.4 Hz, 1H), 3.45 (ddd, J=12.5, 10.8, 4.4 Hz, 1 H), 3.78 (ddd, J=12.1, 4.4, 2.4 Hz, 1H), 4.29 (ddd, J=12.1, 10.8, 3.6 Hz, 1H), 4.51 (d, J=14.5 Hz, 1H), 4.73 (d, J=14.5 Hz, 1H), 5.40 (s, 1H), 5.76 (br s, 1H), 7.26–7.37 (m, 5H); $^{13}$C NMR (100 MHz, $CDCl_3$) δ45.6, 49.9, 57.6, 90.5, 127.9, 128.3 (2C), 128.9 (2C), 135.6, 167.3

$^1$H NMR [400 MHz, $(CD_3)_2SO$] δ3.10 (ddd, J=12.4, 3.8 2.0 Hz, 1H), 3.34 (ddd, J=12.4, 11.2, 4.8 Hz, 1 H), 3.68 (ddd, J=12.0, 4.8, 2.0 Hz, 1H), 4.10 (ddd, J=12.0, 11.2, 3.8 Hz, 1H), 4.46 (d, J=14.8 Hz, 1H), 4.55 (d, J=14.8 Hz, 1H), 5.06 (d, J=6.2 Hz, 1H), 7.15 (d, J=6.2 Hz, 1-OH), 7.23–7.36 (m, 5H); $^{13}$C NMR [100 MHZ, $(CD_3)_2SO$] δ46.0, 49.1, 56.6, 90.6, 127.8, 128.1 (2C), 129.0 (2C), 137.2, 166.2.

EXAMPLE 2

3,5-Bis(trifluoromethyl)bromobenzene

| Materials | MW | Density | Amount | Mmol | Equiv. |
|---|---|---|---|---|---|
| 1,3-Bis(trifluoromethyl)benzene | 214.1 | 1.38 | 107 g | 500 | 1.0 |
| 96% $H_2SO_4$ | | | 142 mL | | |
| Glacial HOAc | | | 22 mL | | |
| 1,3-Dibromo-5,5-dimethylhydantoin | 285.93 | | 77.25 g | 270 | 1.08 ($Br^+$) |
| 5N Aq NaOH | | | 75 mL | | |

A vigorously stirred solution of 1,3-bis(trifluoromethyl)benzene (107 g) in a mixture of glacial acetic acid (22 mL) and concentrated sulfuric acid (142 mL) was added 1,3-dibromo-5,5-dimethylhydantoin (77.25 g) at 25° C. The exothermic reaction raised the temperature to approximately 40° C. After aging at 45° C. for 4.5 h, the mxture was cooled to approximately 0° C. and poured into cold water (250 mL). After washing with 5N NaOH (75 mL) the organic layer contained 137 g of the desired 3,5-bis(trifluoromethyl)-1-bromobenzene by assay (94% yield). This product was used in the next step without further purification.

EXAMPLE 3

1-(3,5-Bis(trifluoromethyl)phenyl)ethan-1-one

| Materials | MW | Density | Amount | Mmol | Equiv |
|---|---|---|---|---|---|
| 3,5-Bis(trifluoromethyl)-bromobenzene | 293.03 | 1.699 g/L | 29.3 g | 98.0 | 1.0 |
| Magnesium granules, 20 mesh | 24.3 | | 5.10 g | | 2.1 |
| Acetic Anhydride | 102.1 | 1.08 g/L | 40 mL | 423 | 4.5 |

-continued

| Materials | MW | Density | Amount | Mmol | Equiv |
|---|---|---|---|---|---|
| THF (KF = 60 μg/mL) | | | 260 mL | | |
| MTBE | | | 650 mL | | |
| Water | | | 300 mL | | |
| 50% NaOH | | | 40 mL | | |

A solution of 3,5-Bis(trifluoromethyl)bromobenzene (29.3 g) in 30 mL of THF was added to a mixture of magnesium granules (5.10 g) in THF (200 mL) heated at reflux (the reaction was initiated with approximately 5 mL of the bromide solution; the remainder was added slowly over 1 h). Alternatively, the Grignard initiation may be conducted at 0–20° C. to minimize the loss of solvent. The mixture was aged for 30 min at reflux, cooled to RT and added over 1 h to a solution of acetic anhydride (40 mL) in THF (40 mL) maintained at −15° C. The resulting dark brown mixture was warmed to 10° C. in a water bath, and water (300 mL) was added. The pH of the vigorously stirred biphasic mixture was adjusted to 8.0 using 50% NaOH. MTBE (300 mL) was added, the layers were separated and the aqueous layer was further extracted with MTBE (3×150 mL). The organic layers were combined and concentrated in vacuo (bath at 30–35° C.; 50–80 torr). The concentrate was then distilled at atmospheric pressure to provide the pure product (20.7 g; 82% yield) with a boiling point of 187–189° C.

EXAMPLE 4

(R)-1-(3,5-Bis(trifluoromethyl)phenyl)ethan-1-ol

| | | | |
|---|---|---|---|
| 1-(3,5-Bis(trifluoromethyl)-phenyl)ethan-1-one | 256.15 | 3.9 | 1 Kg |
| (Cp*RhCl$_2$)$_2$ | 618.08 | 0.01 | 6 g |
| (Cp* = Pentamethylcyclopentadienyl) | | | |
| (S,R)-cis-Aminoindanol | 149.20 | 0.02 | 3.0 g |
| NaOH | 5N (H$_2$O) | 0.05 | 9 mL |
| IPA | | | 7 L |
| HCl | 1N (H$_2$O) | | 7 L |
| Heptane | | | 7 L |
| 1,4-diazabicyclo[2.2.2]octane (DABCO) | 112.18 | 2.2 | 240 g |

A solution of [Cp*RhCl$_2$]$_2$ (Cp* = pentamethylcyclopentadienyl; 6.0 g), (1S,2R)-cis-1-amino-2-indanol (3.0 g) and 1-(3,5-Bis(trifluoromethyl)phenyl)ethan-1-one (1.0 kg) in 2-propanol (7 L) was stirred for 30 min and thoroughly degassed under vacuum. Then 5 M sodium hydroxide (9 mL) was added and the mixture was aged for 3–4 h to achieve complete conversion of the starting material. The reaction mixture was poured into 1 N HCl (7 L) and extracted with heptane (2×3.5 L). The combined organic layers were washed with brine (5 L) and 1,4-diazabicyclo[2.2.2]-octane (240 g) was added. The solution was concentrated to approximateky 4 mL/g of alcohol (KF<200 μg/mL; 2-propanol <5 vol %). The mixture was seeded at 40° C., allowed to cool to RT to form a seedbed and then cooled to 0° C. The crystalline product was filtered, washed with cold heptane and dried to provide the DABCO complex (70% yield; e.e.>99%).

EXAMPLE 5

(R)-1-(3,5-Bis(trifluoromethyl)phenyl)ethan-1-ol

| Materials | MW | Mol | Amt |
|---|---|---|---|
| 1-(3,5-Bis(trifluoromethyl)-phenyl)ethan-1-one | 256.15 | 11.7 | 3 Kg |
| [RuCl$_2$(p-cymene)]$_2$ (Cym = p-cymene (4-isopropyltoluene)) | 612.40 | 0.03 | 18.4 g |
| (S,R)-cis-Aminoindanol | 149.20 | 0.06 | 9.0 g |
| NaOH | 5N (H$_2$O) | 0.14 | 28 mL |
| IPA | | | 21 L |
| HCl | 1N (H$_2$O) | | 21 L |
| Heptane | | | 21 L |
| 1,4-Diazabicyclo[2.2.2]octane (DABCO) | 112.18 | ~6.6 | ~740 g |

A solution of [RuCl$_2$(p-cymene)]$_2$ (18.4 g), (1S,2R)-cis-1-amino-2-indanol (9.0 g) and 1-(3,5-bis(trifluoromethyl) phenyl)ethan-1-one (3 kg) in 2-propanol (21 L) was stirred for 30 min and thoroughly degassed under vacuum. Then 5 M sodium hydroxide (28 mL) was added and the mixture was aged for 4–6 h to achieve complete conversion of the starting material. The reaction mixture was poured into 1 N HCl (21 L) and extracted with heptane (2×10.5 L). The combined organic layers were washed with brine and 1,4-diazabicyclo[2.2.2]octane (740 g) was added. The solution was concentrated to approximateky 4 mL/g of alcohol (KF<200 µg/mL; 2-propanol<5 vol %). The mixture was seeded at 40° C., allowed to cool to RT to from a seedbed and then cooled to 0° C. The crystalline product was filtered, washed with cold heptane and dried to provide the DABCO complex (75–80% yield; e.e.>99%).

EXAMPLE 6

(2R, 2-alpha-R)-4-Benzyl-2-[1-[3,5-bis(trifluoromethyl)phenyl]ethoxy-1,4-oxazin-3-one (Process 1)

| Materials | Kg | L | mol | MW | density | mol % |
|---|---|---|---|---|---|---|
| 4-Benzyl-2-hydroxy-1,4-oxazin-3-one | 2.14 | | 10.3 | 207.2 | | 100 |
| Trifluoroacetic anhydride | 2.16 | 1.46 | 10.3 | 210.0 | 1.487 | 100 |
| (R)-(3,5-bis(trifluoro-methyl)phenyl)ethan-2-ol (49.5 wt % solution in acetonitrile) | 5.11 | 5.13 | 9.80 | 258.2 | 0.996 | 95 |
| Boron trifluoride etherate | 0.73 | 0.65 | 5.14 | 141.9 | 1.120 | 50 |
| 5N NaOH(aq) | 7.60 | 38.0 | | | 370 | |
| 3,7-Dimethyloctan-3-ol | 4.90 | 5.93 | 31.0 | 158.3 | 0.826 | 300 |
| Potassium t-butoxide (solid) | 0.75 | | | 112.2 | | 65 |
| Acetic acid (neat) | 0.62 | 0.59 | 10.3 | 60.05 | 1.049 | 100 |
| Acetonitrile | | 5.3 | | | | |
| Heptane | | 27 | | | | |
| 5% Sodium bicarbonate (aq) | | 5 | | | | |
| Water | | 23 | | | | |

Trifluoroacetic anhydride (2.16 kg) was added over 10 min to a dry (KF<100 µg/mL) slurry of lactam lactol (2.14 kg) in acetonitrile (5 L) cooled at 5° C. The temperature rose from 5 to 30° C. and the solids dissolved. The solution was aged for 1 h between 17–25° C. before a concentrated solution of (R)-(3,5-bis(trifluoromethyl)phenyl)ethan-2-ol in acetonitrile (5.11 kg of solution containing 2.53 kg of alcohol) was added followed by BF$_3$ etherate (0.65L). The temperature rose from 17 to 27° C. and the mixture was aged for 4 h before 5 M NaOH (7.6 L) was added slowly while maintaining the temperature below 27° C. followed by 3,7-dimethyloctan-3-ol (5.9 L). The resulting mixture was distilled at atmospheric pressure until the vapor temperature reached 92° C. and most of the acetonitrile was distilled off. Water (5 L) and heptane (8 L) were added and the mixture was warmed to 45° C. The organic layer was separated, washed with water (13 L) at 45–50° C. and then diluted with heptane (16 L). The solution was dried via an azeotropic distillation until KF<130 µg/mL (6 L of distillate collected; 3 L of fresh heptane added). The solution was cooled to RT and seeded with the (R,R) diastereomer (50 mg). Upon formation of a seedbed the slurry was cooled to –10° C. and potassium tert-butoxide (752 g) was added in one portion. The mixture was aged between –12 and –7° C. for 8.5 h when virtually all of the undesired diastereomer had been converted to the desired (R,R) diastereomer according to HPLC analysis. Acetic acid (0.59 L) was added followed by a 5% NaHCO$_3$ in water solution (5 L). The biphasic mixture was warmed to 45–50° C. The organic layer was separated, washed with water (5 L) at 45–50° C. and concentrated via distillation at atmospheric pressure to a total volume of 24

L (12 L of distillate collected). Upon cooling to 35° C. a seedbed formed. The slurry was cooled to −10° C. and then filtered. The solids were washed with cold heptane (4.5 L) and dried in vacuo to provide (2R, 2-alpha-R)-4-benzyl-2-[1-[3,5-bis (trifluoromethyl)phenyl]ethoxy-1,4-oxazin-3-one (3.66 kg; 83% overall yield).

EXAMPLE 7

(2R, 2-alpha-R)-4-Benzyl-2-[1-[3,5-bis (trifluoromethyl)phenyl]ethoxy-1,4-oxazin-3-one (Process 2)

| Materials | Kg | L | mol | MW | density | mol % |
|---|---|---|---|---|---|---|
| 4-Benzyl-2-hydroxy-1,4-oxazin-3-one | 2.03 | | 9.80 | 207.2 | | 100 |
| Trifluoroacetic anhydride | 2.06 | 1.38 | 10.3 | 210.0 | 1.487 | 100 |
| (R)-(3,5-bis(trifluoromethyl)phenyl)ethan-2-ol (49.5 wt % solution in acetonitrile) | 4.85 | 4.87 | 9.30 | 258.2 | 0.996 | 95 |
| Boron trifluoride etherate | 0.69 | 0.62 | 4.86 | 141.9 | 1.120 | 50 |
| 5N NaOH(aq) | | 8.1 | 40.5 | | | 410 |
| 3,7-Dimethyloctan-3-ol | | 1.68 | 2.03 | 10.6 | 158.3 | 0.826 |
| Potassium 3,7-dimethyl-oct-3-oxide (48.7 wt % in heptane, 1.99M) | 1.09 | 1.36 | 2.70 | 196.4 | 0.803 | 28 |
| Acetic acid (neat) | 0.28 | 0.29 | 4.66 | 60.05 | 1.049 | 47 |
| Acetonitrile | | 4.8 | | | | |
| Heptane | | 21 | | | | |
| 5% Sodium bicarbonate (aq) | | 4.1 | | | | |
| Water | | 20.4 | | | | |

Trifluoroacetic anhydride (2.056 kg) was added over 10 min to a dry (KF<140 μg/mL) slurry of lactam lactol (2.03 kg) in acetonitrile (4.8 L) cooled at 5° C. The temperature rose from 5 to 34° C. and the solids dissolved. The solution was aged for 1 h between 17–25° C. before a concentrated solution of (R)-(3,5-bis(trifluoromethyl)phenyl)ethan-2-ol in acetonitrile (4.85 kg of solution containing 2.40 kg of alcohol) was added followed by $BF_3$ etherate (0.62 L). The temperature rose from 17 to 28° C. and the mixture was aged for 2 h before 5 M NaOH (8.1 L) was added slowly while maintaining the temperature below 27° C., followed by 3,7-dimethyloctan-3-ol (2.0 L). The resulting mixture was distilled at atmospheric pressure until the vapor temperature reached 92° C. and most of the acetonitrile was distilled off (8.1 L of distillate collected). Water (4.1 L) and heptane (12.2 L) were added and the mixture was warmed to 45° C. The organic layer was separated, washed with water (12.2 L) at 45–50° C. and then diluted with heptane (6 L). The solution was dried via an azeotropic distillation until KF<130 μg/mL (7.8 L of distillate collected). The solution was cooled to RT and seeded with the (R,R) diastereomer (50 mg). Upon formation of a seedbed the slurry was cooled to −110° C. and potassium 3,7-dimethyloct-3-oxide (1.09 kg; 48.7 wt % solution in heptane) was over 10 min. The mixture was aged between −12 and −7° C. for 5 h during which virtually all of the undesired diastereomer had been converted to the desired (R,R) diastereomer according to HPLC analysis. Acetic acid (0.28 L) was added followed by a 5% $NaHCO_3$ in water solution (4.1 L). The biphasic mixture was warmed to 45–50° C. The organic layer was separated, washed with water (4.1 L) at 45–50° C. and concentrated via distillation at atmospheric pressure to a total volume of 16 L (4.1 L of distillate collected). The solution was seeded at 45° C. and then allowed to cool to RT. The slurry was cooled to 5° C., aged for 1.5 h and then filtered. The solids were washed with cold heptane (3.0 L) and dried in vacuo to provide (2R, 2-alpha-R)-4-benzyl-2-[1-[3,5-bis(trifluoromethyl)phenyl]ethoxy-1,4-oxazin-3-one (3.51 kg; 84% overall yield).

Melting point: 92–93° C.

$^1$H NMR (400 MHz, $CDCl_3$) δ7.97 (s, 2H), 7.83 (s, 1H), 7.31 (m, 5H), 5.05 (q, J=6.6 Hz, 1H), 4.82 (s, 1H), 4.69 (d, J=14.6 Hz, 1H), 4.58 (d, J=14.6 Hz, 1H), 4.32 (ddd, J=12.0, 11.6, 3.6 Hz, 1H), 3.78 (ddd, J=11.8, 4.7, 1.2 Hz, 1H), 3.48 (ddd, J=12.0, 4.8, 1H), 3.09 (ddd, J=12.2, 3.6, 1.4 Hz, 1H), 1.57 (d, J=6.5 Hz, 3H).

$^{19}$F NMR (376 MHz, $CDCl_3$) δ-63.3 (s).

$^{13}$C NMR (100 MHz, $CDCl_3$) δ163.6, 145.2, 135.7, 131.8 (q, J=33.7 Hz), 128.7, 128.2, 127.7, 126.8 (m), 123.3 (q, J=272.7 Hz), 121.5 (sep, J=4.0 Hz), 94.1, 73.8, 57.1, 49.6, 45.2, 24.1.

A specific crystalline form of (2R, 2-alpha-R)-4-benzyl-2-[1-[3,5-bis (trifluoromethyl)phenyl]ethoxy-1,4-oxazin-3-one is characterized by virtue of its X-Ray Powder Diffraction (XRPD) pattern. The XRPD pattern was collected on a Philips PW 3710 MPD control automated powder diffractometer. The x-ray generator employed a copper target, an accelerating potential of 45 kV and a filament emission of 40 mA. Diffraction patterns were collected from 2 to 40 degrees.

This polymorphic form of (2R, 2-alpha-R)-4-benzyl-2-[1-[3,5-bis (trifluoromethyl)phenyl]ethoxy-1,4-oxazin-3-one was characterized by an X-ray powder diffraction pattern with key reflections at approximately: 18.89, 20.69, 21.53, 22.50 and 23.04° (2 theta).

Figure 1:
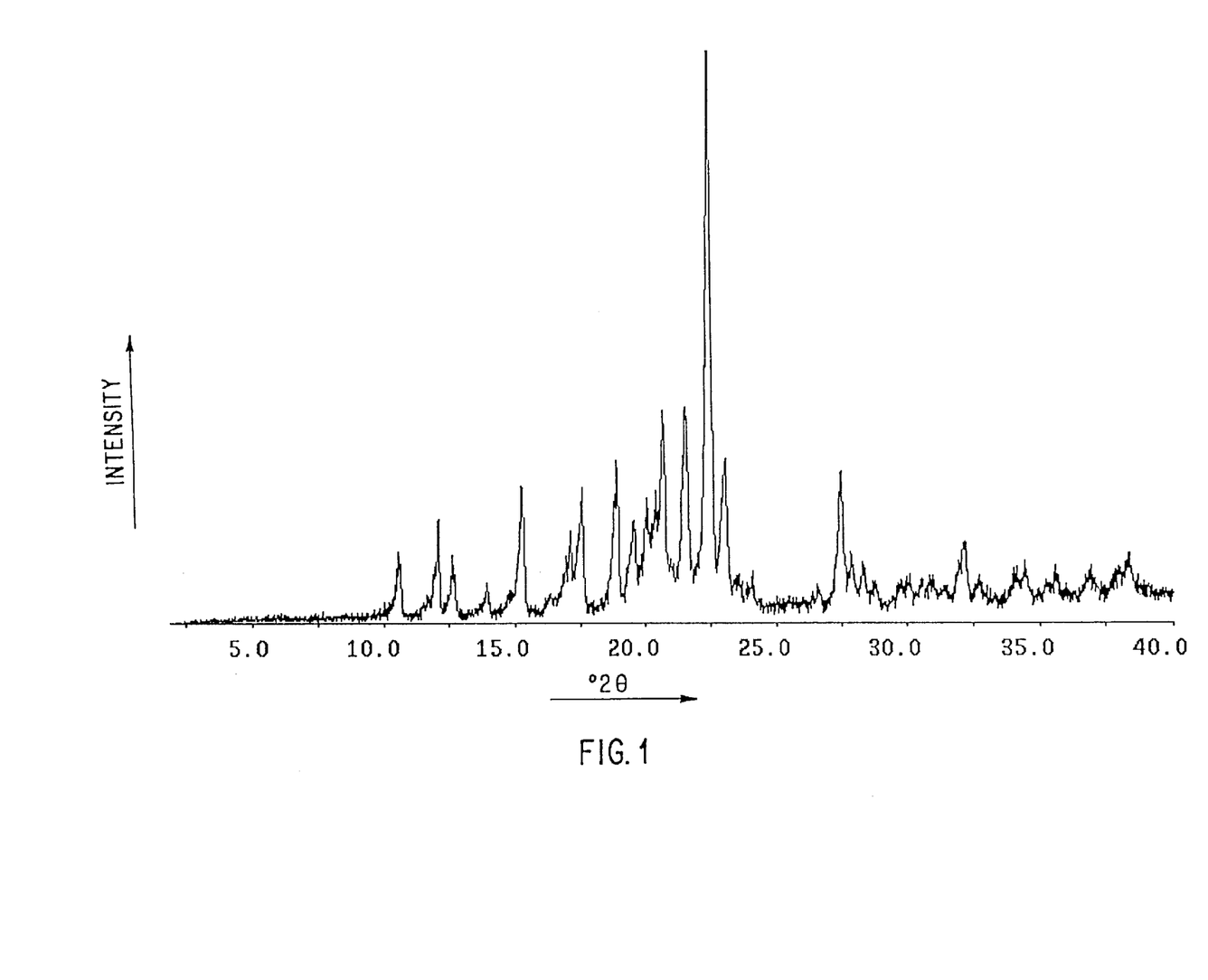
FIG. 1 is an X-ray powder diffraction pattern of Form I of (2R, 2-alpha-R)-4-benzyl-2-[1-[3,5-bis(trifluoromethyl)phenyl]ethoxy-1,4-oxazin-3-one.

Additional XRPD data pertaining to this polymorphic form is presented below (Generator settings: 45kV, 40 mA; Cu alpha1, 2 wave lengths 1.54439, 1.54439 Ang) and in FIG. 1.

TABLE 1

| Peak No. | D Spacing (Ang) | I/Imax (%) |
|---|---|---|
| 1 | 8.33 | 9.50 |
| 2 | 7.33 | 18.33 |
| 3 | 6.99 | 9.29 |
| 4 | 6.35 | 5.58 |
| 5 | 5.79 | 22.99 |
| 6 | 5.18 | 14.98 |
| 7 | 5.05 | 21.69 |
| 8 | 4.69 | 27.10 |
| 9 | 4.68 | 23.32 |
| 10 | 4.53 | 16.61 |
| 11 | 4.42 | 18.33 |
| 12 | 4.29 | 36.33 |
| 13 | 4.12 | 37.16 |
| 14 | 3.95 | 100.00 |
| 15 | 3.86 | 28.54 |
| 16 | 3.78 | 5.75 |

TABLE 1-continued

| Peak No. | D Spacing (Ang) | I/Imax (%) |
| --- | --- | --- |
| 17 | 3.24 | 22.99 |
| 18 | 3.19 | 8.47 |
| 19 | 3.14 | 7.32 |
| 20 | 2.78 | 11.26 |
| 21 | 2.63 | 5.26 |
| 22 | 2.60 | 6.42 |
| 23 | 2.52 | 5.11 |
| 24 | 2.34 | 7.32 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, reaction conditions other than the particular conditions as set forth herein above may be applicable as a consequence of variations in the reagents or methodology to prepare the compounds from the processes of the invention indicated above. Likewise, the specific reactivity of starting materials may vary according to and depending upon the particular substituents present or the conditions of manufacture, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A process for the preparation of a compound of the formula:

which comprises:

activation of the 2-hydroxy group of 4-benzyl-2-hydroxy-1,4-oxazin-3-one of the formula:

coupling of the activated 4-benzyl-2-hydroxy-1,4-oxazin-3-one with (R)-1-[3,5-bis(trifluoromethyl)-phenyl]ethan-1-ol of the formula:

in the presence of a Lewis acid; and crystallization driven epimerization of the anomeric center, to give the compound of the formula:

2. The process of claim 1 wherein the activating agent is trifluoroacetic anhydride.

3. The process of claim 1 wherein the Lewis acid is selected from boron trifluoride etherate, TMSOTf, titanium tetrachloride, tin tetrachloride.

4. The process of claim 1 wherein the Lewis acid is boron trifluoride etherate.

5. The process of claim 1 wherein the crystallization driven epimerization of the anomeric center is conducted with a base selected from potassium or sodium hydroxides or alkoxides derived from a lower ($C_1$–$C_5$) or higher ($>C_6$) primary, secondary or tertiary alcohol in an alcohol and a cosolvent which is a non-polar $C_5$–$C_{12}$ alkane.

6. The process of claim 1 wherein the crystallization driven epimerization of the anomeric center is conducted with potassium 3,7-dimethyloct-3-oxide and potassium t-butoxide in a solvent which comprises a mixture of 3,7-dimethyloctan-3-ol and heptane.

7. A compound which is:

8. A polymorphic form of a compound of the formula:

which is characterized by an X-ray powder diffraction pattern with key reflections at approximately: 18.89, 20.69, 21.53, 22.50 and 23.04° (2 theta).

* * * * *